United States Patent [19]

Corrin

[11] Plant 4,874

[45] Aug. 10, 1982

[54] GRAPE VINE

[76] Inventor: Allan A. Corrin, 6541 S. Holbrook, Reedley, Calif. 93654

[21] Appl. No.: 215,670

[22] Filed: Dec. 12, 1980

[51] Int. Cl.[3] ..... A01H 5/03

[52] U.S. Cl. ..... Plt./47

[58] Field of Search ..... Plt./47

*Primary Examiner*—Robert E. Bagwill

*Attorney, Agent, or Firm*—Huebner & Worrel

[57] ABSTRACT

A grape vine generally similar to the Black Rose grape vine (unpatented), but distinguished therefrom by being of more vigorous growth and by bearing grapes which mature about 30 days later, which have superior shipping characteristics, and which ripen more evenly so that each grape of the new variety is more uniformly and darkly colored than grapes of the Black Rose variety.

1 Drawing Figure

BACKGROUND OF THE NEW VARIETY

The present invention relates to a new and distinct variety of grape vine, which is generally similar to the Black Rose Grape vine (an unpatented variety developed by the U.S. Department of Agriculture), but is more vigorous and which bears grapes having a darker and more uniform skin coloration and a tougher skin which provides superior shipping qualities, the new variety being especially characterized by bearing grapes which ripen about 30 days later than grapes of the Black Rose variety.

As in fresh fruits of all kinds, it is important that table grapes reach the consumer in good condition and it is highly desirable that the grapes have a pleasing color. Commercial success of a variety of plants bearing relatively perishable fruit is greatly enhanced if the plant bears fruit at a season when generally similar fruits are not available. A large size and superior flavor are, of course, desirable characteristics of table grapes as well as other fruits.

There are several varieties of grape vines bearing large so-called black grapes for table use, one of the best known being the Ribier or Alphonse Lavallee variety (unpatented) and another being the Black Rose variety (unpatented). The Ribier grape vine is noted for its bearing of grapes which are of a uniform dark color and of large size and which ship well. However, the grapes of this variety are somewhat lacking in flavor. On the other hand, grapes borne by the Black Rose variety have a superior flavor to those of the Ribber variety and are even larger in size. However, the skin of grapes borne by the Black Rose variety of grape vine is relatively tender and is thus not adapted for shipment to relatively distant markets. Further, bunches of the Black Rose variety do not ripen evenly so that the coloration of individual berries is undesirable in that all berries do not attain a uniform black color, some being streaked with reddish-purple and others having substantial areas which are greenish in color.

Therefore, it is recognized as being highly desirable to provide a grape vine bearing fruit similar in size and black coloration to those borne by the Black Rose and Ribier varieties and which ships well, has a desirable flavor, and has berries of large size and of a substantially uniform, dark coloration. It has long been known that such a variety of grape vine would be particularly desirable if its fruit ripened at a time substantially later in the season than the fruit of other grape vines bearing large dark grapes.

ORIGIN AND ASEXUAL REPRODUCTION OF THE NEW VARIETY

The new variety of grape vine was discovered by me in 1975 as a seedling on my farm near the intersection of Frankwood and Goodfellow Avenues near the City of Reedley, in the County of Fresno, in the State of California.

For many years, I have cross-pollinated grape blossoms, or had them cross-pollinated, obtained the resultant seeds, and grown seedlings produced from such seeds all in a vineyard on my designated farm with a view toward developing improved varieties of grape vines. The subject variety grape vine originated as a seedling from cross-pollination between grape vine varieties on my farm; however, the records of the parent grape vines involved in such cross-pollination and the resulting seedlings were inadvertently destroyed in 1963 and the parental source of the new variety is unknown.

The new variety was asexually reproduced by me by cuttings in 1978 on my designated farm, and the fruit and vine characteristics resulting from the cuttings proved identical to those of the original seedling.

SUMMARY OF THE NEW VARIETY

The instant variety of grape vine is generally characterized by bearing fruit of large size and blunted elliptical shape, the fruit having a skin which is substantially black and bears a heavy but easily removed grayish-blue bloom. The new variety is also generally characterized by having leaves of extremely large size, the length and width of the leaves being about 240 mm.

The new variety of grape vine most nearly resembles the Black Rose (unpatented) variety but is distinguished therefrom in three important ways. First, the grapes borne by the new variety ripen approximately 30 days later than the grapes borne by the Black Rose variety. Second, the skin of grapes borne by the new variety is substantially tougher than that of the Black Rose variety. Third, the stems of the individual grapes borne by the new variety, sometimes called "cap stems", are substantially heavier and more firmly attached to the grape than are stems of grapes of the Black Rose variety. The new variety is, therefore, superior in shipping and storage characteristics to the Black Rose variety.

Finally, the skin color of fruit of the new variety is substantially a solid and uniformly dark in contrast to that of the Black Rose, which is frequently striped with reddish-purple with many berries shading toward the base to reddish-purple and even to light yellow green.

Further comparing the new variety with the Black Rose variety, the berries of the new variety have relatively blunt ends and are somewhat smaller. Under comparable growing conditions, the length and diameter of grapes of the new variety average 21 mm and 28 mm, respectively, while the corresponding dimensions of the Black Rose variety average, respectively, 23 mm and 30 mm. Each berry of the new variety typically has two mature and one immature seed, while berries of the Black Rose variety typically have two or three mature seeds. The new variety of grape vine is further distinguished from the Black Rose by being more vigorous and by the above-mentioned larger leaves.

In comparison with the well-known Ribier or Alphonse Lavallee (unpatented) variety of grape vine, the fruit of the new variety has a superior flavor and the berries are substantially larger and are substantially elongated. Under comparable growing conditions, berries of the Ribier variety are nearly spherical, having a length and diameter averaging, respectively, 25 mm and 32 mm, while the corresponding dimensions of berries of the new variety are 21 mm and 28 mm. The skin of berries of the Ribier variety is a solid dark color while the skin of a small minority of the grapes of the new variety has a dark reddish-purple cast and/or a narrow annulus of dark purple about the stem. The skin of fruits of the new variety is tougher than the skin of the Ribier variety, and the skin of the latter variety lacks the heavy bloom of the new variety. Each berry of the Ribier variety, typically, has one or two mature seeds in contrast to the new variety in which each berry, typically, has two mature seeds and one immature seed as before stated.

BRIEF DESCRIPTION OF THE DRAWING

The accompanying drawing is a color photograph of a bunch of mature grapes of the subject variety together with a pair of representative leaves and with two grapes which are divided to show the flesh color and seed arrangement and are disposed adjacent to a scale.

DETAILED DESCRIPTION

Referring more specifically to the pomological details of this new and distinct variety of grape vine, the following has been observed under the ecological conditions prevailing in the above-designated farm near Reedley, Calif. All color code plate identifications and color names in quotation marks are by reference to the Maerz and Paul *Dictionary of Color,* Second Edition, published in 1950 by the McGraw-Hill Book Company, Inc., other color names being common descriptive names.

VINE

Size: Large.

Growth: Vigorous, more vigorous than the Black Rose variety (unpatented).

Productivity: Heavy and regular.

Canes:

*Thickness.*—Stout.

*Joints.*—Average spacing.

*Tendrils.*—Medium in thickness, length, abundance, and strength.

Foliage: Many leaves, the leaves being of extremely large size — average width 220 mm, average length 225 mm, the largest specimen measured having a width of 280 mm and a length of 250 mm.

*Color.*—At time of harvest of the fruit, upperside from "Parrot Green" (21 L 6) to dark yellow green (24 J 3) on older leaves; lowerside, greenish-yellow (21 J 3).

*Margin.*—Shallow indentations.

Flowers: Average in number and similar in form and color to those of the Black Rose variety; blooming season 7 to 10 days.

FRUIT

Maturity: About 30 days after the Black Rose variety, approximately Oct. 15 on the above-identified farm; ripening a bit early, on Oct. 8 in 1980.

Size of grapes: Large; diameter from 16 mm to 23 mm, average 21 mm; length from 23 mm to 34 mm, average 28 mm.

Average number of bunches to vine: 30 to 40.

Number of seeds to grape: Typically two mature and one immature seeds per grape.

Skin: Tight; tougher than skin of Ribier variety (unpatented).

Color:

Skin.—Substantially black, darker than any sample of plates 48 or 56, with heavy, easily wiped-off blush of "Hussar" (38 D 9); some berries lightening toward base to narrow, 1 mm or 2 mm in width, annulus of dark reddish-purple (47 L 5).

*Flesh.*—Similar to Black Rose with berry divided longitudinally and centrally and skin otherwise intact; very light greenish-yellow (19 B 2) between seeds on longitudinal centerline and, peripherally, light olive (21 F 2).

Bunches ripen: Evenly.

Texture: Medium.

Flavor: Superior to Ribier.

Shipping quality: Excellent.

Storing quality: Excellent.

Use: Fresh table.

Although the new variety of grape vine bears the described characteristics as a result of the growing conditions in Fresno County, Calif., in the central part of the San Joaquin Valley, it is to be understood that variations of the usual magnitude in characteristics incident to growing conditions, fertilization, pruning, and pest control are to be expected.

Having thus described and illustrated my new variety of grape vine, what is new and desired to be secured by Letters Patent is:

1. A new and distinct variety of grape vine, substantially as illustrated and described, characterized by its resemblance to the Black Rose grape vine (unpatented), which it most nearly resembles, in bearing fruit of large size having a dark, approximately black skin, the new variety being characterized as to novelty by having leaves of extremely large size and berries having a heavy bluish-gray bloom and by being distinguished from the Black Rose variety in that the new variety is of more vigorous growth and bears fruit which matures about 30 days later, has superior shipping qualities due to a tougher skin and heavier stem, and being further distinguished from the Black Rose variety by more even ripening of each bunch so that each berry of the new variety has a skin color which is substantially solidly and uniformly dark except for a small annulus about the stem.

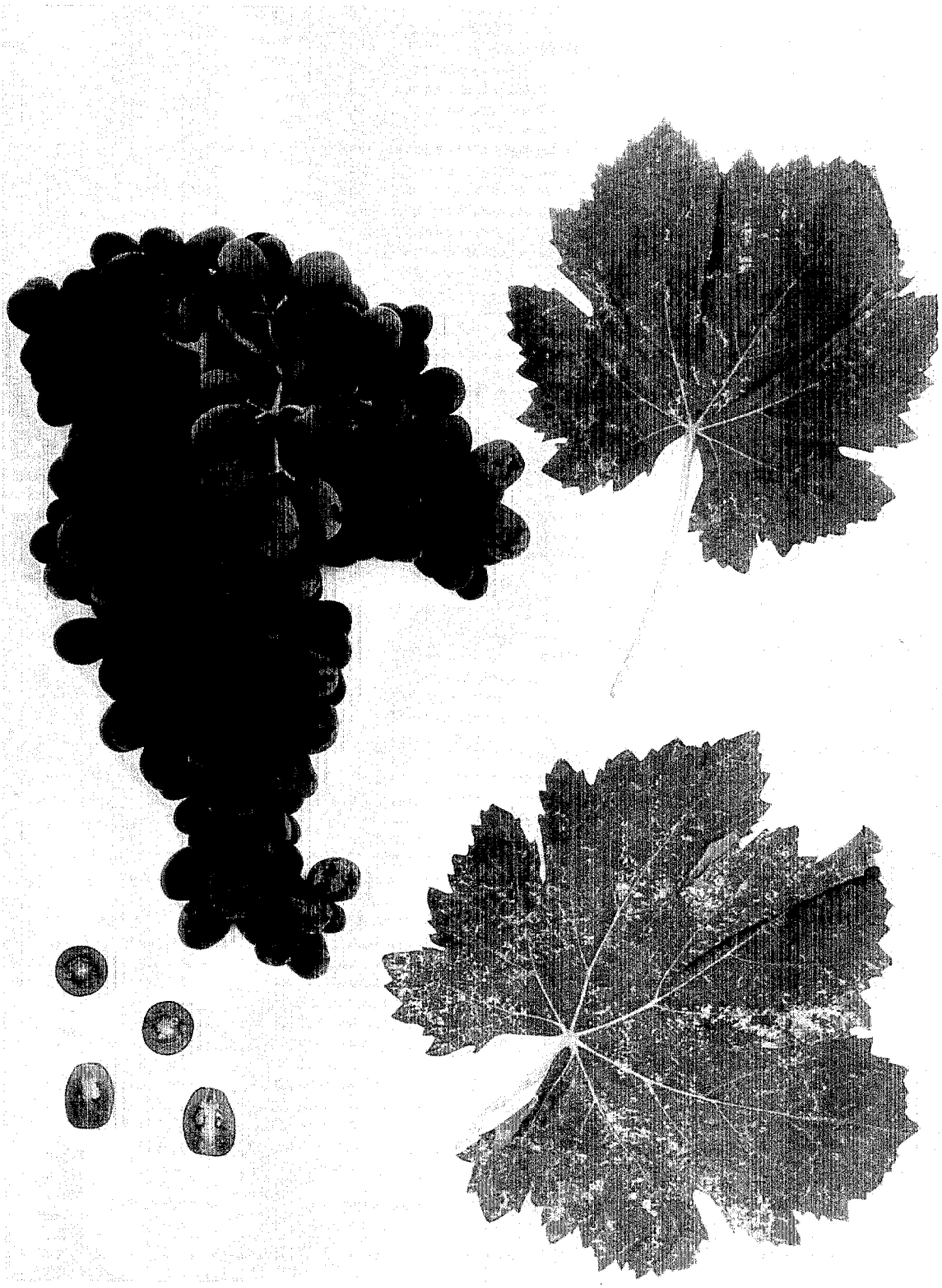

* * * * *